United States Patent
Angus et al.

(10) Patent No.: US 7,814,805 B2
(45) Date of Patent: Oct. 19, 2010

(54) AUTOMATED PIPETTE MACHINE

(75) Inventors: Andrew Angus, Pearcedale (AU); Fred Davis, Canterbury (AU); Adam Donath, Richmond (AU); Richard Grant, St. Kilda (AU); Dirk Kurpershoek, Seaford (AU)

(73) Assignee: Stemcell Technologies Inc., Vancouver (CA)

( * ) Notice: Subject to any disclaimer, the term of this patent is extended or adjusted under 35 U.S.C. 154(b) by 47 days.

(21) Appl. No.: 12/164,209

(22) Filed: Jun. 30, 2008

(65) Prior Publication Data

US 2009/0007703 A1    Jan. 8, 2009

Related U.S. Application Data

(62) Division of application No. 11/182,741, filed on Jul. 18, 2005, now abandoned.

(60) Provisional application No. 60/588,331, filed on Jul. 16, 2004.

(51) Int. Cl.
*G01N 1/14* (2006.01)
*G01N 35/10* (2006.01)
*B01L 3/02* (2006.01)

(52) U.S. Cl. .................... 73/864.14; 73/864.22; 422/64

(58) Field of Classification Search .................. None
See application file for complete search history.

(56) References Cited

U.S. PATENT DOCUMENTS

| 553,044 A | 1/1896 | Sharples |
|---|---|---|
| 2,768,493 A | 10/1956 | Holler |
| 3,444,742 A | 5/1969 | Ellis et al. |
| 3,827,304 A | 8/1974 | D'Autry |
| 4,501,497 A | 2/1985 | Nanba |
| 4,748,859 A | 6/1988 | Magnussen et al. |
| 4,779,768 A | 10/1988 | St. Amand |
| 4,961,350 A | 10/1990 | Tennstedt |

(Continued)

FOREIGN PATENT DOCUMENTS

JP    59188538 A * 10/1984 .................. 422/100

(Continued)

*Primary Examiner*—Thomas P Noland
(74) *Attorney, Agent, or Firm*—Lucas & Mercanti, LLP

(57) ABSTRACT

A pipette nozzle is provided for use on a movable arm on an automated pipette machine. The pipette nozzle includes a body defining a passage therethrough and having at least two seating surfaces provided on the body. The first seating surface is configured to receive and sealingly mate with a first size of pipette tip in a manner such that the first end of the passage is in fluid communication with the first size of pipette tip. The second seating surface is configured to correspondingly receive, sealingly mate and provide passage first end fluid communication with a second size of pipette tip. There is also provided an automated pipette machine which includes a tip ejector system including an arm that is movable between a first position and a second position wherein in the first position the arm is positioned to engage the tip during movement of the nozzle along a selected path and to prevent movement of the tip along the selected path while permitting the nozzle to move along the selected path, so that the movement of the nozzle along the selected path causes the nozzle and the tip to disengage from each other, and wherein in the second position the arm is positioned to avoid engagement with the tip during movement of the nozzle.

8 Claims, 12 Drawing Sheets

U.S. PATENT DOCUMENTS

| | | | |
|---|---|---|---|
| 5,389,339 A * | 2/1995 | Petschek et al. | 422/64 |
| 5,439,649 A * | 8/1995 | Tseung et al. | 422/99 |
| 6,116,099 A | 9/2000 | Carl | |
| 6,596,240 B2 | 7/2003 | Taggart et al. | |
| 6,793,891 B2 | 9/2004 | Yiu | |
| 6,874,379 B2 | 4/2005 | Matsuda et al. | |
| 7,033,543 B1 | 4/2006 | Panzer et al. | |
| 7,047,828 B2 | 5/2006 | Blaszcak et al. | |
| 7,267,801 B2 * | 9/2007 | Hitch et al. | 422/64 X |
| 2001/0039843 A1 | 11/2001 | Schoeppe | |
| 2002/0028565 A1 | 3/2002 | Nikolaev et al. | |
| 2002/0053245 A1 | 5/2002 | Carl | |
| 2002/0092367 A1 | 7/2002 | Bell | |
| 2003/0000319 A1 | 1/2003 | Rainin et al. | |
| 2003/0082078 A1 | 5/2003 | Rainin et al. | |
| 2008/0264187 A1 * | 10/2008 | Angus et al. | 73/864.14 |
| 2008/0295618 A1 * | 12/2008 | Angus et al. | 73/864.14 |
| 2009/0007703 A1 | 1/2009 | Angus et al. | |

FOREIGN PATENT DOCUMENTS

| | | | | |
|---|---|---|---|---|
| JP | 03202773 A | * | 9/1991 | 422/100 |
| JP | 08094506 A | * | 4/1996 | |
| JP | 09192825 A | * | 7/1997 | |

* cited by examiner

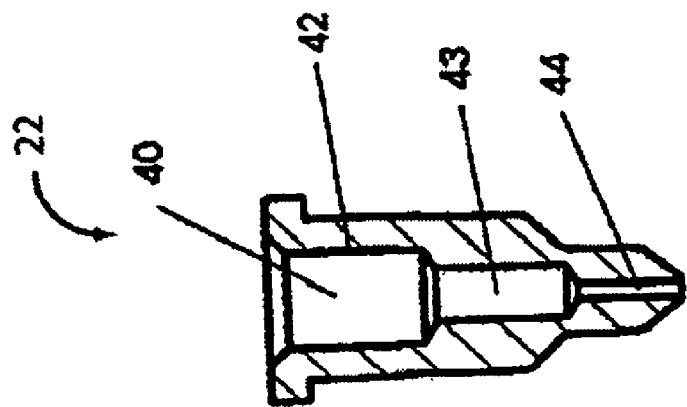
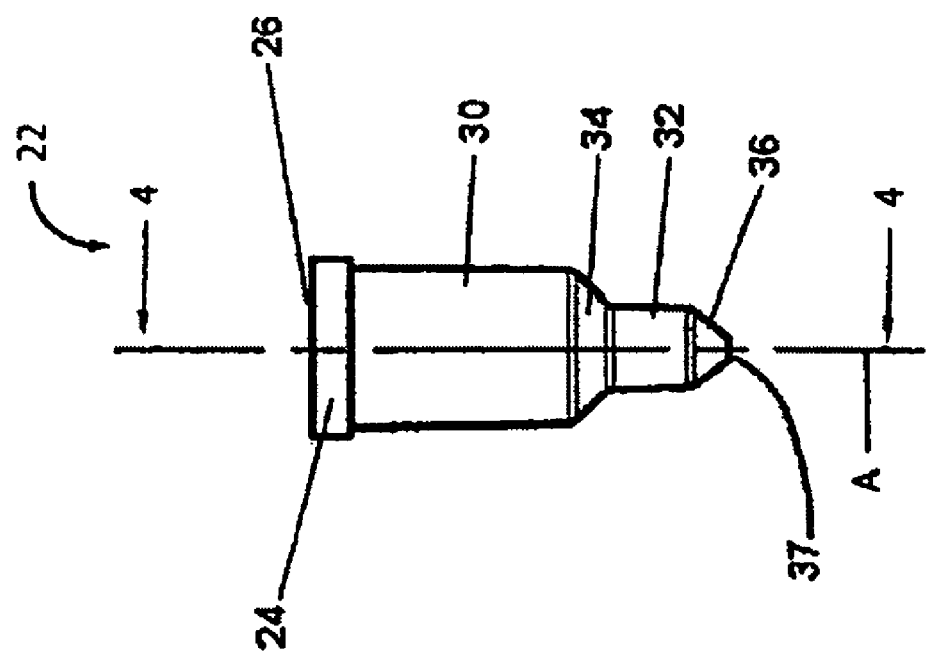

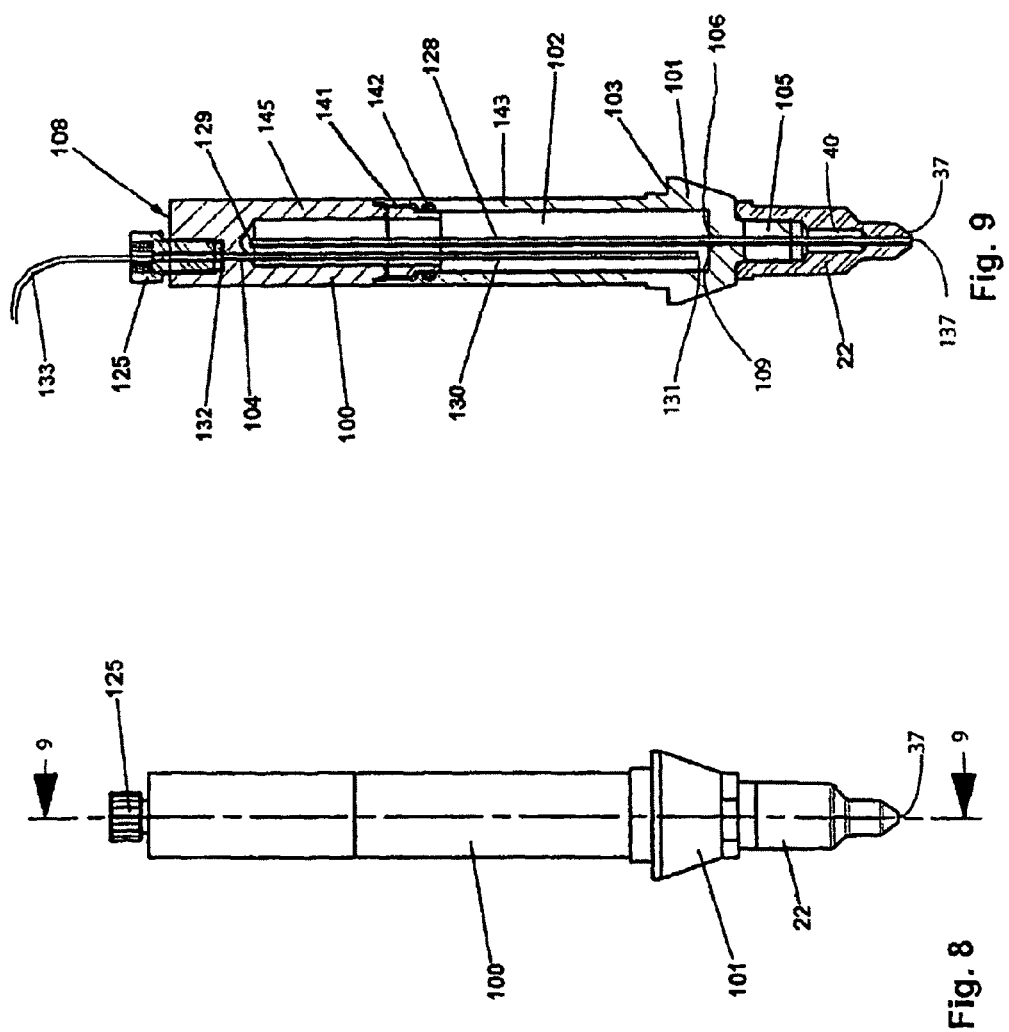

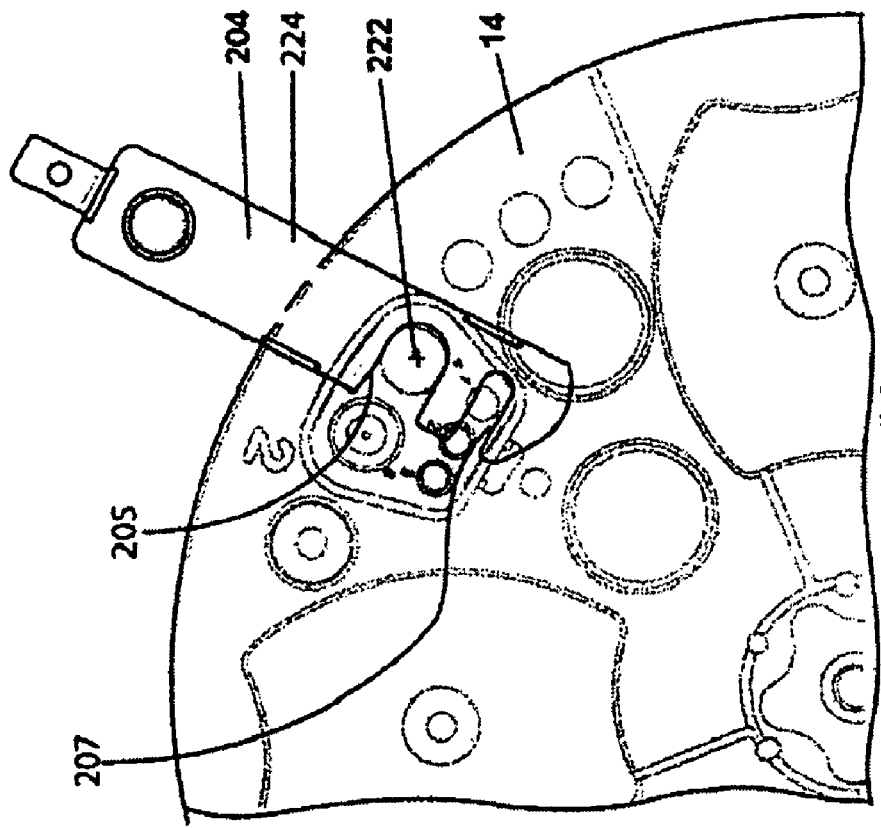
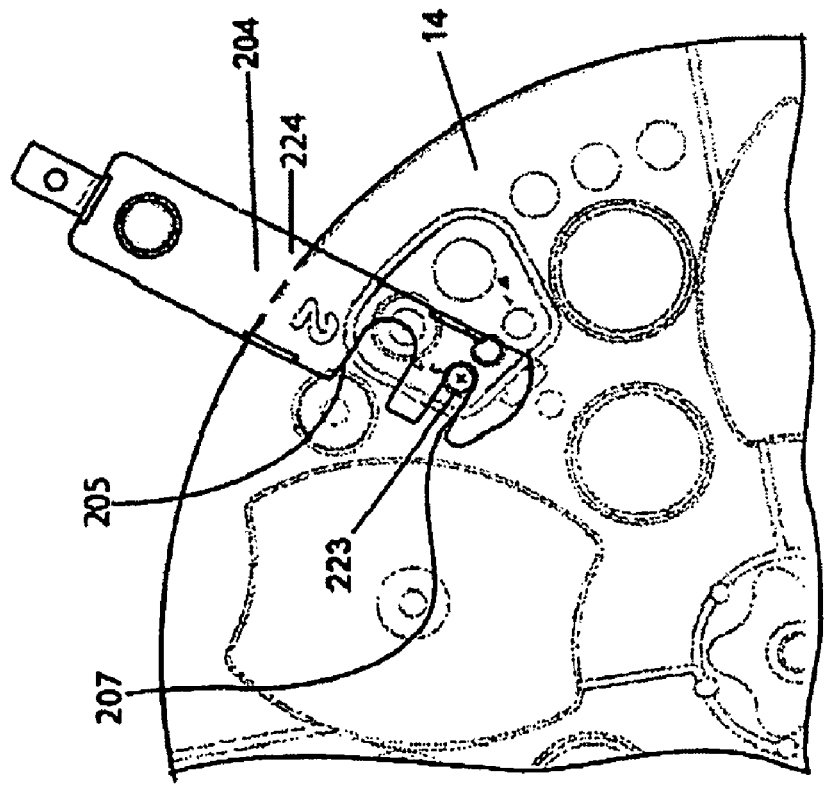

AUTOMATED PIPETTE MACHINE

This application is a division of co-pending U.S. application Ser. No. 11/182,741 filed on Jul. 18, 2005, which in turn is a Parent, which claims the benefit of U.S. Provisional Application No. 60/588,331 filed on Jul. 16, 2004. The entire disclosure of the prior application is hereby incorporated by reference herein in its entirety.

FIELD OF THE INVENTION

This invention relates generally to automated apparatus for handling chemical and biological fluids, and more particularly to automatic pipette machines.

BACKGROUND OF THE INVENTION

Automatic pipette machines or robots are used in the chemical and biological fields to automatically pipette fluids from one place to another, without the need for direct human involvement. Generally, automated pipette robots have three axes of motion to allow a moveable tip head to access different containers with fluid samples in a given area. One class of robots are known as θ-z-θ robots which combine rotational (θ) and vertical (z) motion of a robot arm holding the tip head with rotational (θ) motion of a carousel that holds the samples, thereby allowing the tip head to access the samples on the carousel. A more common class of robots are x-y-z gantry style robots (e.g. BioMek FX™, Qiagen™ Biorobots™) where the moveable tip head moves along one vertical axis and two orthogonal horizontal axes of motion. To avoid contamination, many automatic pipette machines use disposable pipette tips. Typically, the tip head on these robots has one or more nozzles that receive a pipette tip.

Typically, the tip heads on the automated pipette robots can accommodate only one size of disposable pipette tip. However, a given size of pipette tip is best suited for pipetting a limited range of volumes of fluid. Some processes require that a wider range of volumes of fluid be transferred from one place to another than can be accommodated by the tip. In such instances, either the pipette head must make multiple trips between the source and destination locations in order to cumulatively transfer the required volume, or human intervention is required to transfer the volumes that cannot be effectively handled by the pipette machine. It would be desirable to provide an automated pipette machine capable of pipetting a wider range of volumes.

Automated pipette systems often use a hydraulic fluid in the fluid lines that connect the pump to the pipette tip head because hydraulic fluids are less compressible than air. As the liquid volume in the pipette tip increases, the pressure drop between the pump and the tip head increases. It is easier to calibrate the pump to attain the desired pipette volume accuracy if most of the volume in the line between the pump and the tip head is a hydraulic fluid. In addition, for positive displacement pumps, the volume of liquid the pump can draw into the tip with a single piston stroke is higher using a hydraulic fluid.

Existing automated pipette technology is limited to aspirating a maximum of approximately 1 mL of liquid. In these machines, there is tubing of a relatively small diameter and of sufficient length between the tip head and the pump to accommodate up to 1 mL of air displaced from the pipette tip during aspiration. Small diameter tubing is used so that if there is an interface between hydraulic fluid and air in a section of the tubing that is not horizontal, the hydraulic fluid does not flow down into the air volume. If this occurs, then air can be inadvertently introduced into the pump, causing a loss of volumetric dispensing accuracy. Many analysis processes require that volumes significantly greater than 1 mL be pipetted. To pipette larger volumes of fluid a longer tube can be used while maintaining the diameter of the tube constant so that the tube remains small enough in cross-section so that no air is inadvertently introduced into the pump during operation.

A longer tube, however, has several drawbacks associated with it. For example, in a long length of tubing there is an increased chance that as the hydraulic fluid is drawn into the pump, there will be breaks at the air-hydraulic fluid interface resulting in the formation of discrete bubbles between the main interface and the nozzle. When the pump initiates the dispensing step, these bubbles will be ahead of the main interface and may be expelled from the nozzle, contaminating the tip and potentially contaminating the fluid that the tip aspirated, and the fluid volume into which the tip is dispensing. Additionally, a long length of tubing provides increased pressure drop at a given fluid flow-rate, which in turn, means that pump cavitation would occur at a relatively lower flow-rate during aspiration. Furthermore, the increased pressure drop reduces the maximum dispensing flow-rate. Another drawback is that, for both the aspirating and dispensing steps, the higher pressure drop through a long length of tubing may increase the chance of leakage at connections between the different tubes, the pump, and the nozzle, since higher (or lower) initial pressures are required at the pump to achieve operation.

These drawbacks associated with longer tubing as described above also apply to the use of small diameter tubing for 1 ml machines that are currently in use. In other words, for any machine that incorporates a length of relatively small diameter tubing which functions as a reservoir for air during operation, the above described problems are present.

It would be desirable to have a system that can transfer volumes of fluid without incorporating long hydraulic fluid lines.

Another drawback related to current automated pipette machines relates to the disposal of used pipette tips. There are currently various mechanisms proposed and in use for removing disposable pipette tips from the pipette nozzle. However, many of these mechanisms are relatively intricate, thereby increasing the complexity of the pipette machines and the cost of manufacture. Furthermore, many of the devices of the prior art eject the pipette tip in an uncontrolled manner, usually into a disposal bin, thereby making it impractical to reuse the tip if desired. For example, in some analysis techniques, the same material is transferred in non-consecutive steps, in which case reuse of the tip is desirable since contamination is not an issue. It would be desirable to have a pipette machine that is capable of reusing a pipette tip.

SUMMARY OF THE INVENTION

In a first aspect, the invention is directed to a pipette nozzle for use on a movable arm on an automated pipette machine. The pipette nozzle includes a body defining a passage therethrough. The pipette nozzle includes a connecting portion on the body for connecting the pipette nozzle to the movable arm. There are provided at least two seating surfaces on the body, including a first seating surface and a second seating surface. The first seating surface is configured to receive and sealingly mate with a first size of pipette tip in a manner such that the passage is in fluid communication with the first size of pipette tip. The second seating surface is configured to receive and sealingly mate with a second size of pipette tip in a manner such that the passage is in fluid communication with the second size of pipette tip.

In a second aspect, the invention is directed to an apparatus for use on an automated pipette machine for transmitting pressure changes produced by a pump on the machine to a pipette nozzle. The apparatus includes a housing defining a chamber. The apparatus further includes a first conduit extending into the chamber and having a first opening positioned in the chamber. The first conduit is fluidically connectible to the nozzle. The apparatus further includes a second conduit extending into the chamber and having a first opening positioned in the chamber, wherein the second conduit is fluidically connectible to the pump. The first opening of the first conduit is positioned above the first opening of the second conduit. The chamber defines at least a selected volume between the height of the first opening of the first conduit and the height of the first opening of the second conduit.

In a third aspect, the invention is directed to a tip ejector system for use on an automated pipette machine to eject a pipette tip from a pipette nozzle on the machine. The tip ejector system includes an arm that is movable between a first position and a second position. In the first position the arm is positioned to engage the tip during movement of the nozzle along a selected path thereby preventing movement of the tip along the selected path while permitting the nozzle to move along the selected path, so that the movement of the nozzle along the selected path causes the nozzle and the tip to disengage from each other. In the second position the arm is positioned to avoid engagement with the tip during movement of the nozzle.

In a fourth aspect, the invention is directed to an automated pipette machine including a movable carousel having a plurality of pipette receptacles, a movable pipette machine arm with a pipette nozzle attached thereto, and a tip ejector system. The pipette nozzle includes a body defining a passage therethrough and at least two seating surfaces on the body, including a first seating surface and a second seating surface. The first seating surface is configured to receive and sealingly mate with a first size of pipette tip in a manner such that the passage is in fluid communication with the first size of pipette tip. The second seating surface is configured to receive and sealingly mate with a second size of pipette tip in a manner such that the passage is in fluid communication with the second size of pipette tip. The tip ejector system includes a tip ejector arm that is movable between a first position and a second position, wherein in the first position the tip ejector arm is positioned to engage the tip during movement of the nozzle along a selected path and to prevent movement of the tip along the selected path while permitting the nozzle to move along the selected path, so that the movement of the nozzle along the selected path causes the nozzle and the tip to disengage from each other, and wherein in the second position the tip ejector arm is positioned to avoid engagement with the tip during movement of the nozzle.

BRIEF DESCRIPTION OF THE DRAWINGS

For a better understanding of the present invention and to show more clearly how it may be carried into effect, reference will now be made by way of example to the accompanying drawings, in which:

FIG. 3 is a side view of a nozzle of the pipette arm in FIG. 2;

FIG. 4 is a cross-sectional view along section line 4-4 shown in FIG. 3;

FIG. 8 is a side view of a reservoir apparatus of the pipette arm of FIG. 7;

FIG. 9 is a cross-sectional view along section line 9-9 shown in FIG. 8;

FIGS. 14a and 14b are plan views of an ejector arm in alignment with tip compartments on a carousel on the pipette machine of FIG. 1.

DETAILED DESCRIPTION OF THE DRAWINGS

In the accompanying drawings, like numerals indicate the same elements. It will be understood that the present disclosure is an exemplification of the principles of the invention and does not limit the invention to the illustrated embodiments. Therefore, specific details disclosed herein are not to be interpreted as limiting, but rather as a basis for the claims and as a representative basis for teaching one skilled in the art to employ the present invention.

Figure 1:
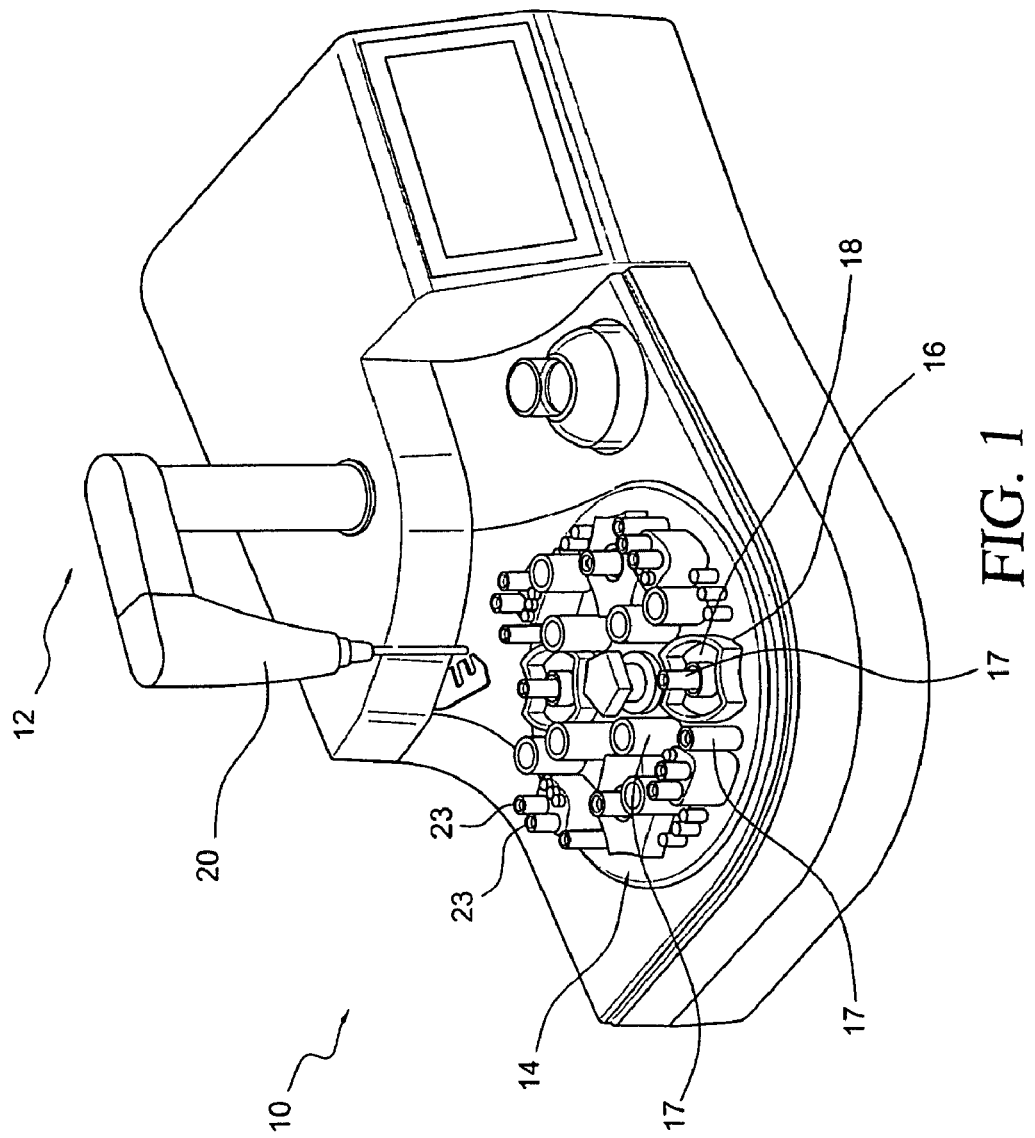
FIG. 1 is perspective view of an automated pipette machine in accordance with an embodiment of the present invention.

Referring to FIG. 1, there is illustrated an automated pipette machine 10, which may also be referred to as an automated pipette robot 10, in accordance with an embodiment of the present invention. The automated pipette machine 10 has a moveable arm 12 and a carousel 14. The carousel 14 has a plurality of apertures 16 of varying size and shape for receiving sample or reagent containers 17, or one or more carriers 18 which are themselves configured to support sample or reagent containers 17. Containers 17 that may be carried by the carriers 18 include, for example, test tubes, vials and the like. Disposable pipette tips 23 may also be provided on the carousel 14 and may be held in one or more carriers 19.

Figure 2:
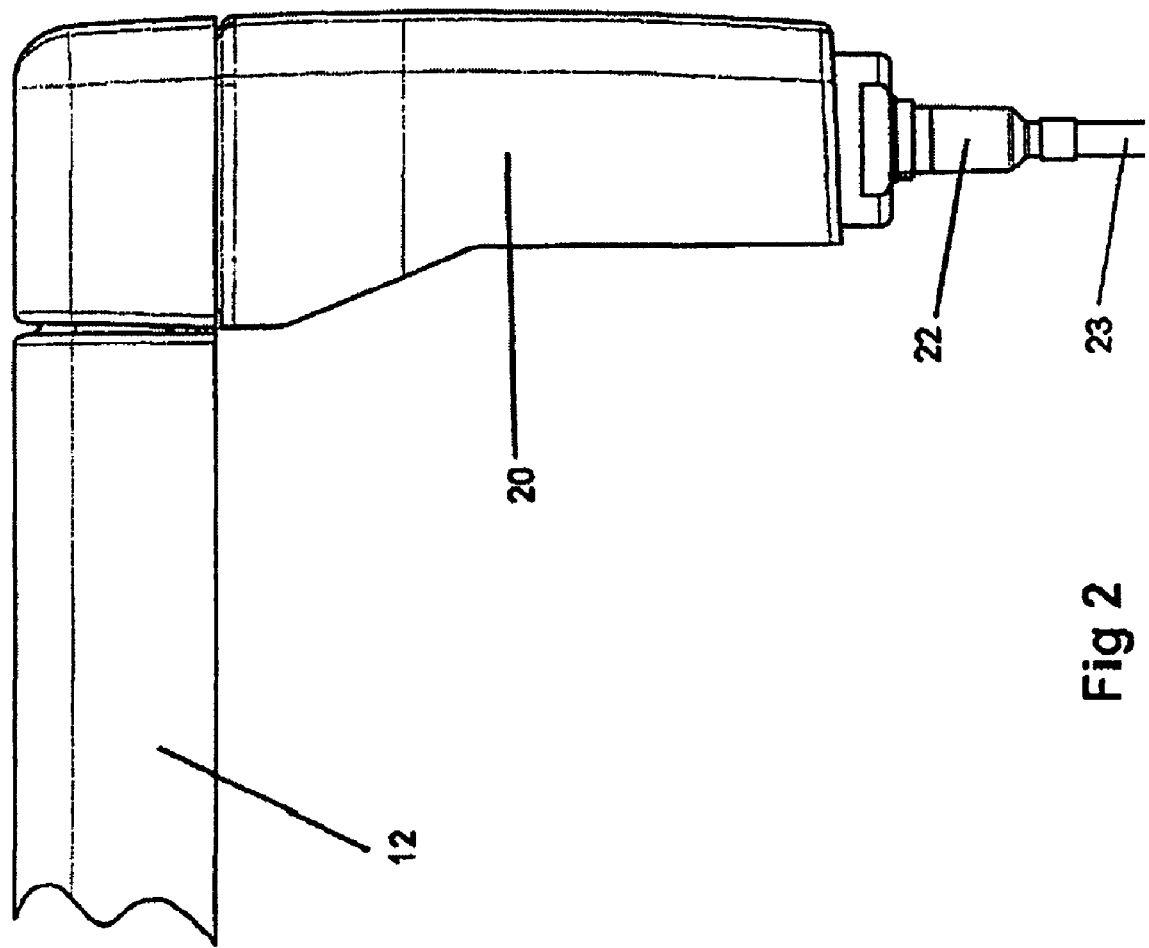
FIG. 2 is a side view of a pipette arm of the machine in FIG. 1.
Figure 15:
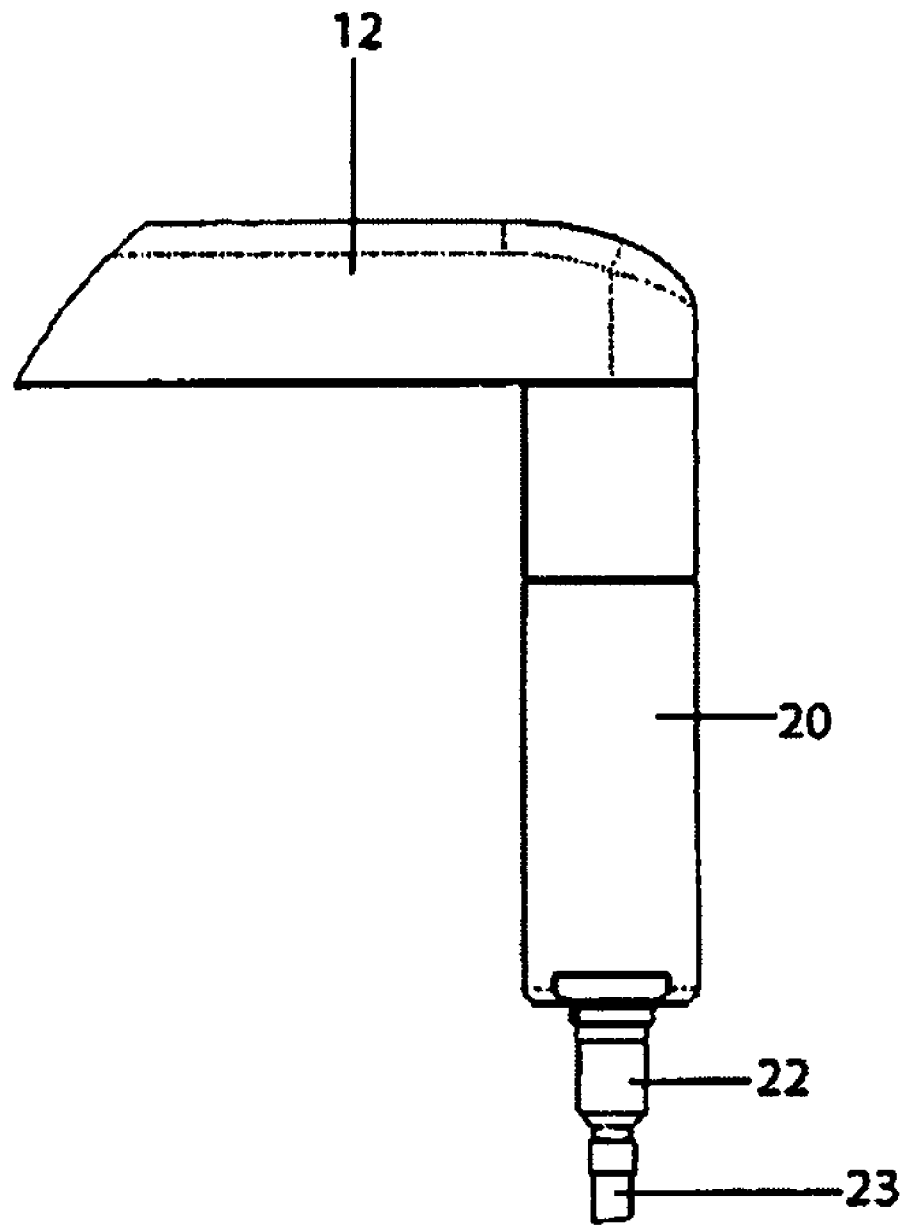
FIG. 15 is a side view of an alternative pipette arm for use with the machine in FIG. 1.

Referring to FIG. 2, arm 12 includes a pipette head 20 upon which is mounted a nozzle 22 for holding a disposable pipette tip 23. Referring to FIG. 1, the machine 10 may move arm 12 and/or carousel 14 in any way known in the art to provide access by the arm 12 to fluid held in the containers 17 on the carousel 14. For example, the pipette machine 10 may be a θ-z-θ robot where the rotational (θ) and vertical (z) motion of the arm 12 is combined with rotational (θ) motion of the carousel 14 to provide access by the arm 12 to containers 17 on the carousel 14 and to dispose the pipette tip 23 in carrier 19 or the carousel 14. Alternatively, the automated pipette machine 10 may, for example, be an x-y-z gantry style machine having an arm that is movable along three orthogonal axes, eg. a vertical axis and two orthogonal horizontal axes. An alternative configuration of the arm 12 is shown in FIG. 15.

Reference is made to FIGS. 3 and 4, which show the pipette nozzle 22. The tip nozzle 22 may connect to the pipette head 20 in any suitable way. For example, the nozzle 22 may include a connecting portion 24 at a first end 26. The connecting portion 24 may, for example, include a bore 42 (FIG. 4), for connecting by press-fit to a corresponding external surface on the pipette head 20.

Figure 6:
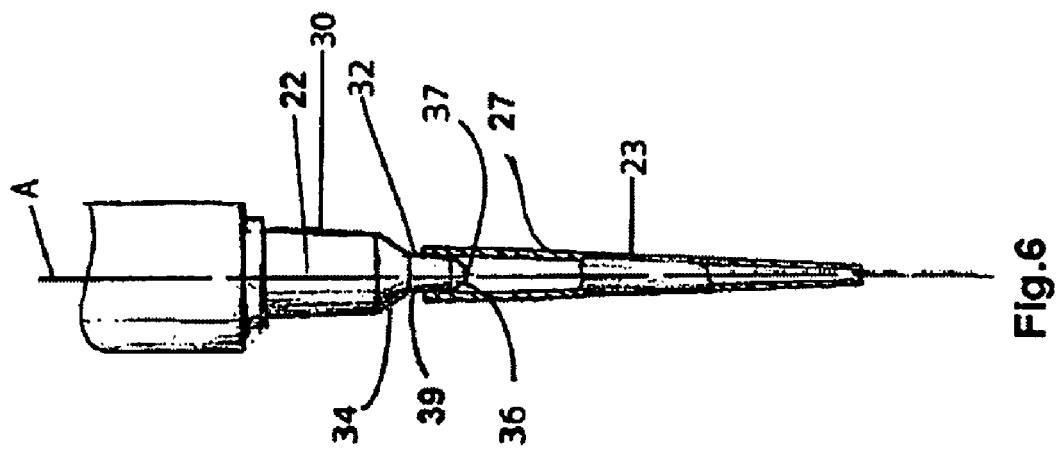
FIG. 6 is a side view of the nozzle shown in FIG. 1, with a second pipette tip mounted thereon.
Figure 5:
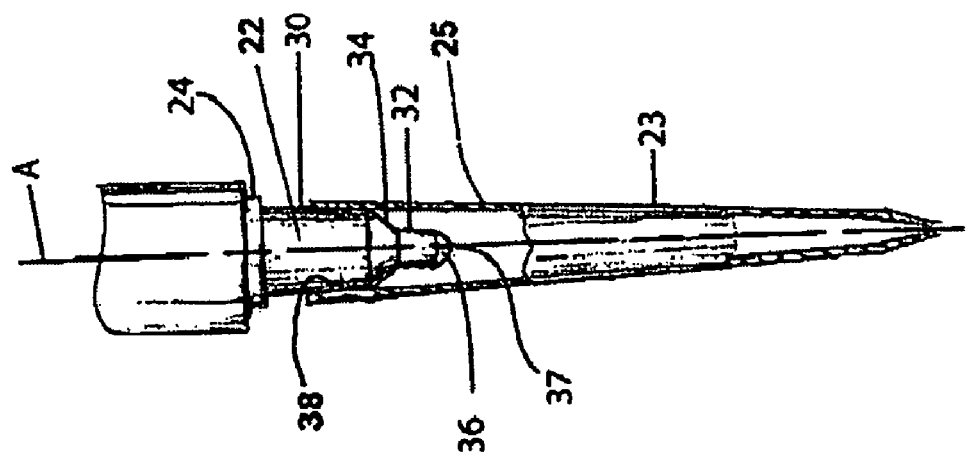
FIG. 5 is a side view of the nozzle shown in FIG. 1, with a first pipette tip mounted thereon.

Reference is made to FIGS. 5 and 6. The nozzle 22 may be sized to hold one or more different sizes of pipette tip 23. For example, the nozzle 22 may be sized to hold a first pipette tip 25 as shown in FIG. 5, and a second pipette tip 27 as shown in FIG. 6. The first tip 25 may have a larger internal volume than the second tip 27, and may thus be sized for holding a relatively greater quantity of fluid than the second tip 27. The first tip 25 has a nozzle-mating end 38, which may have a larger internal cross-section than a nozzle-mating end 39 for the second tip 27. The nozzle-mating ends 38 and 39 of the tips 25 and 27 may be slightly tapered.

The nozzle 22 has a first seating surface 30 and a second seating surface 32, which are configured for receiving the first and second disposable pipette tips 25 and 27 respectively. The first seating surface 30 may be adjacent to the cylindrical portion 24. The second seating surface 32 is sized for receiving the smaller tips 27. The second sealing surface 32 is positioned closer to the end 37 than is the first sealing surface 30. A tapered shoulder 34 separates the first and second seating surfaces 30 and 32. A terminal taper portion 36 is positioned at the distal or remote end 37 of the nozzle 22. Preferably, the first and second seating surfaces 30 and 32 are co-axial; however, they need not be, provided that the transverse cross-sectional periphery of the second seating portion is within the transverse cross-sectional periphery of the first seating portion.

The first seating surface 30 may be frustoconical, having a slight taper towards its axis A in the direction toward the remote end 37 to facilitate insertion of the nozzle 22 into the first pipette tip 25. The interior surface at the nozzle-mating end 38 of the first tip 25 and the first seating surface 30 are configured to sealingly mate together. For example, the large seating portion 32 may be shaped and dimensioned to provide a leak resistant seal with a 5 mL disposable pipette tip such as a 5 mL tip by Macro Tips for Gilson™, Rainin™ and Pipetman™ Pipettors manufactured by USA Scientific.

In similar fashion to the first seating surface 30, the second seating surface 32 may be frustoconical, having a slight taper towards its axis A in the direction toward the remote end 37, which sealingly mates with the interior surface at the nozzle-mating end 39 of the second tip 27. For example, the second seating portion 32 may be configured to provide a leak resistant seal with a 1 mL disposable pipette tip such as a 1100 μL level sensing tip manufactured by Qiagen™, or a 1100 μL tip for Qiagen™ and Rosys™ robots manufactured by USA Scientific. A level sensing tip is not necessary if the instrument is not able to sense liquid levels through the tip head, however tips designed for robotic systems such as the Qiagen™ Biorobots™ have a narrow profile that is useful for accessing fluid at the bottom of relatively full containers without causing the fluid to overflow, or from accessing fluid in narrow, deep containers.

The terms 'leak resistant seal' and 'sealingly mate', which are used throughout this document in connection with the seal between the pipette tip 23 and the nozzle 22 mean that a seal is provided that does not allow air to pass into the pipette tip such that fluid does not inadvertently drip from the tip; or a seal that, if it does allow air to pass into the pipette tip, the rate at which the air passes into the tip is slow enough so that fluid does not inadvertently drip from the tip in the time it takes to transfer the volume of fluid from one vessel to another.

Referring to FIG. 4, a fluid passageway 40 extends through the nozzle 22, and may include the first bore 42, a second bore 43 having a diameter smaller than the first bore 42, and a third bore 44 having a diameter smaller than the second bore 43. The first bore 42 may be used for connecting the nozzle 22 to the pipette head 20 (see FIG. 7). For example, the first bore 42 may be sized to frictionally engage by press-fit the external surface 105 on the pipette head 20.

Reference is made to FIGS. 5 and 6. To acquire a pipette tip 23 for use in a fluid transfer operation, the nozzle 22 and the selected pipette tip 23 are brought into alignment such that the longitudinal axis A of the nozzle 22 is aligned centrally with the open end of the pipette tip 23. The nozzle 22 is moved toward, and inserted into the pipette tip 23 until the tip 23 is firmly seated on the appropriate seating portion 30 or 32 to form a leak resistant seal between the nozzle 22 and the pipette tip 23. The terminal taper 36 serves to guide the pipette tip nozzle 22 into the tip 23 in the event that the nozzle 22 is not precisely aligned with the nozzle-mating end 38 or 39 of the pipette tip 23 during tip acquisition. If the nozzle 22 is being inserted into a first tip 25, the tapered shoulder 34 serves to further guide the nozzle 22 into the tip 25 if they are not precisely aligned.

The embodiment described herein is of a tip head with a nozzle that can accommodate two sizes of pipette tips. However, based on the disclosure of the present invention, it will be appreciated by one skilled in the art that the nozzle of the present invention may be constructed with three or more seating surfaces, to accommodate a corresponding number of sizes of pipette tip 23.

In an alternative embodiment that is not shown, the first and second seating surfaces on the nozzle may alternatively have other shapes than frustoconical. For example, the surfaces may be cylindrical. In embodiments, wherein the first and second seating surfaces are cylindrical, they are preferably provided with 'lead-in' surfaces, which may be a conical or frustoconical shoulder at each of their leading edges to facilitate insertion of the nozzle into a pipette tip. The nozzle-mating ends of the pipette tips may correspondingly be cylindrical, and may optionally be fitted with sealing members therein for sealingly mating with the seating surfaces.

The nozzle 22 may be made from a suitable stainless steel as will be appreciated by one skilled in the art.

Figure 7:
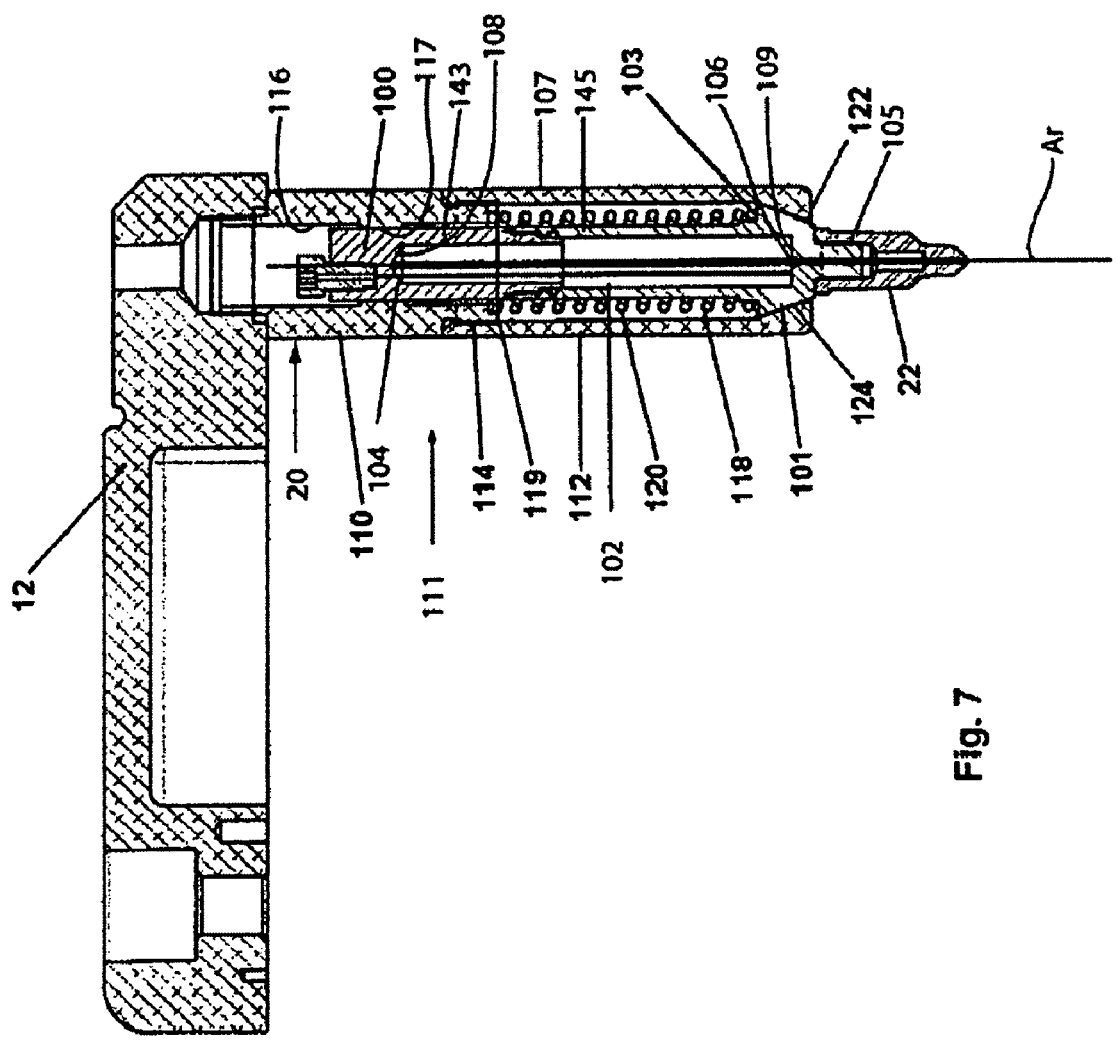
FIG. 7 is a longitudinal cross section of the pipette arm of FIG. 2.

Referring to FIG. 7, the pipette head 20 includes a reservoir system 111 in accordance with another embodiment of the present invention. The reservoir system 111 may include a first housing portion 110 and a second housing portion 112, together forming a housing 107. The reservoir system 111 also includes a fluid reservoir 100, which may be slideably mounted within the housing 107 and may be generally cylindrical in shape. The reservoir 100 has an abutment surface 101, which may be positioned proximate one end. The abutment surface 101 may be frustoconical in shape, tapering to a smaller diameter in a downward direction. It is alternatively possible, however, for the abutment surface 101 to have another shape instead of being frustoconical. For example, the abutment surface 101 may extend in a plane that is transverse to a longitudinal axis Ar of the reservoir 100. The abutment surface 101 mates with a retainer surface 124 on the second housing portion 112 thereby assisting in retaining the reservoir 100 within the housing 107.

The reservoir 100 further includes a shoulder 103 which faces away from the abutment surface 101, and which may be immediately adjacent the abutment surface 101. The shoulder 103 is discussed further below.

The reservoir system 111 further includes a connector surface 105 for connecting with a pipette nozzle, such as nozzle 22, although other suitable nozzles may be used instead of the nozzle 22. When a nozzle, such as nozzle 22 is connected to the pipette head 20, it should be configured so as not to interfere with the motion of the reservoir 100 with respect to the housing 107, which will be described further below.

The reservoir 100 includes a fluid chamber 102, a pump-side port 104 and a pipette-side port 106. Regarding terms of spatial reference used herein, the reservoir 100 in the illustrations should be regarded as being oriented along a vertical axis that is perpendicular to an imagined horizontal surface. Accordingly, the pump side port 104 is located at top or upper end 108 of the reservoir 100, and the pipette-side port 106 is located at bottom or lower end 109 of the reservoir 100.

The first housing portion 110 has an inner surface 116, and the second housing portion 112 has an inner surface 118. The housing portions 110 and 112 may be connected together by any suitable means, such as by a threaded connection 114.

A slide surface 117 slidably receives the reservoir 100. The slide surface 117 may be positioned in the first housing portion 110. The rest of the inner surface 116 may be spaced from the reservoir 100 so that the slide surface 117 is the only portion of the inner surface 116 that contacts the reservoir 100.

The majority of the inner surface 118 is larger than the reservoir 100, and provides sufficient spacing from the reservoir to permit a spring 120 to be positioned around the reservoir 100. The inner surface 118 includes the retainer surface 124 which engages the abutment surface 101 on the reservoir 100 to retain the reservoir 100 in the housing 107.

An internal shoulder 119 is positioned in the housing 107. The shoulder 119 may be defined at the junction between the first and second housing portions 110 and 112.

The spring 120 may be a compression spring which is captured between the internal shoulder 119 and the shoulder 103 on the reservoir 100. The spring 120 thereby exerts a biasing force on the reservoir 100 driving the abutment surface 101 to seat against the retainer surface 124. The spring 120 dampens the forces exerted upon the pipette nozzle 22 and the arm 12 overall as the nozzle 22 is inserted into a pipette tip 23, and facilitates the sealing of the pipette tip 23 onto the nozzle 22. As the robot arm presses the nozzle onto the tip, the spring, which is pre-compressed to exert a force of at least 40 N, preferably 55 N, compresses further, such that the force of the nozzle on the tip does not vary greatly over several mm of vertical travel. In this example the force applied by the nozzle on the tip increases approximately 1.5 N/mm of additional compression of the spring.

Referring to FIG. 9, the pipette-side port 106 communicates with passage 40 of the pipette nozzle 22. Mounted within the pipette-side port 106 and the passage 40 is a first conduit 128, which may be a tube having a first end with a first opening 129 near the upper end 108 of the chamber 102 and having a second end at the remote end 37 of the nozzle 22 or which may extend 1-2 mm beyond the end 37 of the nozzle 22. The first opening 129 of the first conduit 128 is open and in fluid communication with the chamber 102. The first conduit 128 extends through the nozzle to its second end whereat it has a second opening 137 which may be flush with the remote end 37 of the nozzle 22, or which may extend 1-2 mm beyond the end 37 of the nozzle 22. The first conduit 128 provides fluid communication between the chamber 102 and the inside of a pipette tip 23 when one is mounted on the nozzle 22.

Mounted within the pump-side port 104 is a second conduit 130, which may be a tube, which extends into the fluid chamber 102 and has an end with a first opening 131 near the lower end of the chamber 102. The opening 131 provides fluid communication between the second conduit 130 and the chamber 102. To facilitate the assembly of the tubes 128 and 130 within the chamber 102, the reservoir 100 may be made from two portions 143 and 145 which are joined by means of a threaded connection 141. An O-ring seal 142 may be incorporated into the threaded connection to provide an airtight seal between the portions 143 and 145. The second conduit 130 communicates fluidically with a pump (not shown) that provides the pressure differential required for drawing fluid into the pipette tip or expelling fluid therefrom. The other end of the second conduit 130 may communicate with another conduit 133, which is attached to reservoir 100 via a mounting screw 125. The threaded connector (ie. the mounting screw 125), seals with the reservoir 100 by compressing an o-ring between the reservoir 100 and the connector 125.

Referring to FIG. 9, the reservoir 100 includes the pipette-side port 106 which communicates with passage 40 of the pipette nozzle. Mounted within the pipette-side port 106 and the passage 40 is a first conduit 128, which may be a tube, which extends from the remote end 37 of the nozzle 22 into the fluid chamber 102, having an end with a first opening 129 near the upper end of the chamber 102. Accordingly, the first conduit 128 is in fluid communication with the inside of a pipette tip 23 when one is mounted on the nozzle 22. The first opening 129 of the first conduit 128 is open and in fluid communication with the chamber 102. The first conduit 128 has another end which extends through the nozzle 22 and which has a second opening 137 which may be flush with the end 37 of the nozzle 22.

Mounted within the pump-side port 104 is a second conduit 130, which may be a tube, which extends into the fluid chamber 102 and has an end with a first opening 131 near the lower end of the chamber 102. The opening 131 provides fluid communication between the second conduit 130 and the chamber 102. To facilitate the assembly of the tubes 128 and 130 within the chamber 102, the reservoir 100 may be made from two portions 143 and 145 which are joined by means of a threaded connection 141. An O-ring seal 142 may be incorporated into the threaded connection to provide an airtight seal between the portions 143 and 145. The other end of the second conduit 130 communicates fluidically with a pump (not shown) that provides the pressure differential required for drawing fluid into the pipette tip or expelling fluid therefrom. The other end of the second conduit 130 may be positioned for example to communicate with another conduit 133 which is mounted to the reservoir 100 by means of a mounting screw 125, which in turn communicates with the pump.

There are several suitable pumps that would be known to persons skilled in the art, such as, for example, model 3.6/120 or 3.6/265 manufactured by DRD Diluter Corporation. Other pumps that would be suitable include single piston positive displacement pumps such as Series 3500 pumps from Scivex™ with 3.0 or 5.0 mL pump volume and shallow thread pitch. The DRD pump is a dual piston design which allows for accurate low and high volume dispensing, with higher flow-rate high volume dispensing.

Figure 10A:
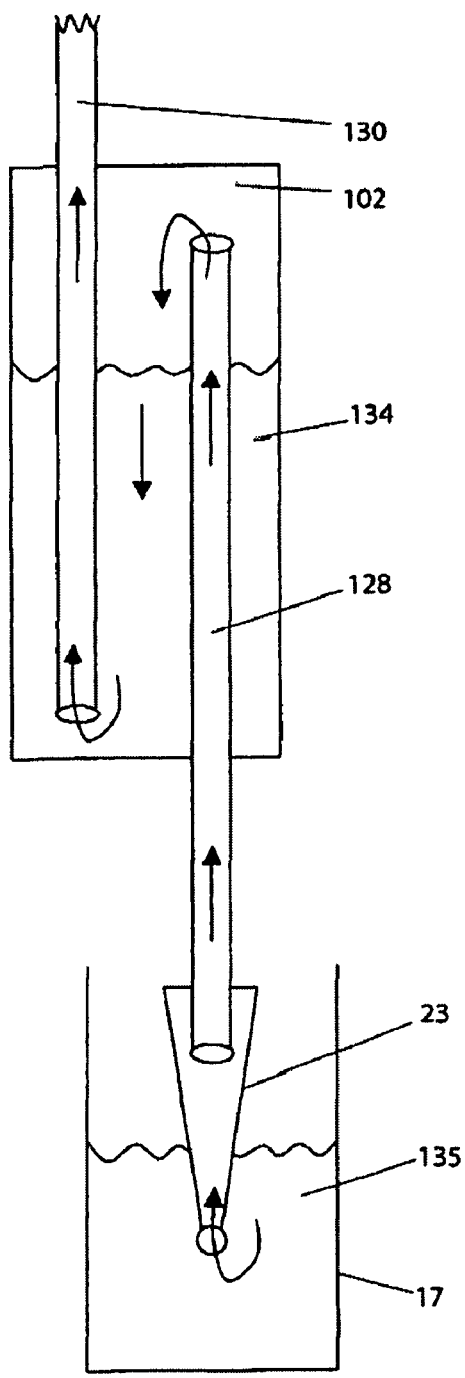
FIGS. 10a and 10b are schematic diagrams of the reservoir apparatus of FIG. 8.
Figure 10B:
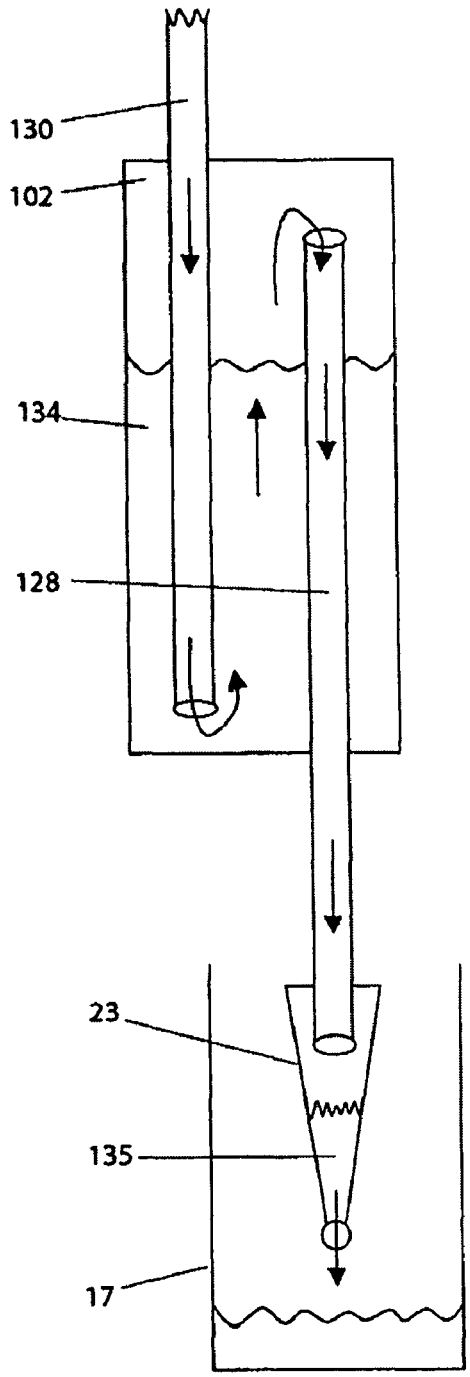

Reference is made to FIGS. 10a and 10b. In operation, the fluid chamber 102 contains a selected volume of hydraulic fluid 134. The volume of the chamber 102 should be selected such that the total volume of hydraulic fluid 134 held in the chamber 102 and the conduits 128 and 130 is greater than the maximum volume to be pipetted. In this way the pump will not draw air into its piston (or into the pumping mechanism if not a piston-type pump). Preferably, the volume in the chamber 102 and tubing 128 and 130 are selected based on the maximum desired fluid handling volume so that there is less fluid wasted during priming which is described below. For example, to handle a maximum volume of 5 mL, the preferred volume of the chamber is and tubing is 6.7 mL.

In order to draw fluid into a pipette tip 23 that is mounted on the pipette nozzle 22, the pump (not shown) is made to apply suction to the second conduit 130 to aspirate a desired volume of hydraulic fluid 134 from the chamber 102. The withdrawal of the fluid 134 from the chamber 102 creates a negative pressure differential between the chamber 102 and the pipette tip 23, and results in fluid 135 being drawn into the pipette tip 23 from a container 17 (see FIG. 1) until an equilibrium in pressure in the system is reached. To expel fluid 135 from the pipette tip 23, the pump is made to apply pressure to the second conduit 130 which injects hydraulic fluid 134 into the chamber 102, creating a positive pressure differential between the chamber 102 and the pipette tip 23, causing the pipette tip 23 to expel fluid 135 until an equilibrium pressure is reached. The volume of hydraulic fluid 134 that is withdrawn from or injected into the chamber 102 is proportional to the volume of fluid 135 that is aspirated into or expelled from the pipette tip 23.

The fluidic system described above comprising tubing 128 and 130 and the reservoir 102 connects the nozzle 22 (FIG. 9b) to the pump (not shown) and attains a known starting condition through a priming action during start-up, and periodic flushing action while performing processes. The need to prime and flush the fluidic system will be understood by those skilled in the art. The nozzle 22 (FIG. 9b) does not hold a tip during priming and flushing actions. The priming action generally consists of a series of steps that are repeated several times. A valve (not shown) to the tubing 130 that connects the pump (not shown) to the pump hydraulic fluid reservoir (not shown) is opened and a valve (not shown) to the nozzle 22 (FIG. 9b) is closed. The hydraulic fluid 134 is preferably sterile deionized water, but can be any other suitable fluid known to those skilled in the art, such as saline solution. A selected volume is drawn into the pump. The valve to the hydraulic fluid is then closed and the valve to the nozzle 22 is opened, and the maximum volume of hydraulic fluid is expelled. Usually three complete cycles of these steps are used to ensure that the complete volume of water in the fluidic system between the nozzle and the pump (not shown) is replaced and that most of the air is displaced from the system between the pump hydraulic fluid reservoir and the nozzle 22, including all of the tubing 128 and 130, the reservoir 100 and the pump (not shown).

Generally, a flushing action is performed after the priming action described above, as well as periodically as needed, to put the system at a known fluidic starting condition. The flushing step consists of drawing a selected volume eg. 500 μL of hydraulic fluid 134 into the pump and then expelling this volume through the nozzle in the same manner as for the flushing operation. The pump then slowly draws in a 200 μL volume of air. This air volume provides a fluidic gap between the nozzle and the hydraulic fluid and serves to reduce the chance that the hydraulic fluid will be expelled into a pipette tip thereby contaminating the tip and potentially contaminating the fluid 135 that the tip aspirates during a fluid manipulation step. The air volume is preferably small relative to the maximum desired pipetting volume to avoid a large compressible volume between the nozzle and pump.

By providing an indirect fluid connection between the pump (not shown) and the nozzle 22 by use of the reservoir system 102 of the present invention, the automated pipette machine 10 is able to handle a wider range of volumes than would otherwise be possible, without having to utilize an extraordinary length of tubing as in devices of the prior art. Fluid handling robots that rely on a continuous length of tubing to hold the air volume displaced from a disposable tip during an aspiration step have several other disadvantages relative to the present system with a reservoir. For example, in a long length of tubing there is an increased chance that as the hydraulic fluid is drawn into the pump, there will be breaks at the air-hydraulic fluid interface resulting in the formation of discrete bubbles between the main interface and the nozzle. When the pump initiates the dispensing step, these bubbles will be ahead of the main interface and may be expelled from the nozzle 22, contaminating the tip 23 and potentially contaminating the fluid that the tip 23 aspirated, and hence the fluid volume into which the tip 23 is dispensing. In a system with a reservoir 100, these bubbles will break in the chamber 102. The combination of relatively short lengths of tubing and the reservoir provide a relatively lower overall pressure drop than a system of the prior art having a similar total internal volume, that relies entirely on small-diameter tubing between the pump and the tip for holding hydraulic fluid and air. Accordingly, the reduced pressure drop in turn reduces the risk of cavitation of the pump at higher flow rates. Further, the system of the present invention can provide higher flow rates for a given pump, or a similar flow rate to prior art systems using relatively lower-performance pumps, which may thus be less expensive, and which may consume less energy. Furthermore, since a selected flow rate can be achieved at a relatively lower pressure drop than for systems of the prior art, the risk of leakage either in or out of the system is reduced.

FIGS. 11-14 show selected components of the pipette machine 10 to illustrate the structure and operation of the tip ejector system 200 in accordance with another embodiment of the present invention. The tip ejector system 200 includes an ejector arm 204 which cooperates with the carousel 14 and the arm 12 during the ejection of a tip 23 from the pipette nozzle 22.

A pipette tip carrier 220 holds one or more sizes of disposable pipette tips 23. For example, the carrier 220 shown in FIG. 11 has a plurality of apertures 222 for holding first tips 25 and a plurality of apertures 223 for holding second tips 27. The tip ejection system described and illustrated herein is adapted to be used with the dual-tip nozzle 22 that is described above. However it will be understood that the tip ejector system 200 may be used with other configurations of nozzles 22, such as, for example, with nozzles that are adapted to receive only one size of tip.

During the operation of acquiring a pipette tip 23 for use in a fluid transfer operation, the nozzle 22 and a pipette tip 23 are brought into alignment by the rotation of the carousel 14 and/or the rotation of the arm 12 such that the nozzle 22 is aligned for insertion into the nozzle-mating end 38 or 39 of the pipette tip 23. The nozzle 22 is then moved toward and inserted into the pipette tip 23 until the tip 23 is firmly seated on the appropriate seating surface—the first seating surface 30 (see FIG. 12d), or the second seating surface 32 (see FIG. 13d)—so as to form a leak resistant seal between the nozzle 22 and the pipette tip 23. The nozzle 22 is then moved away from the carousel 14 which withdraws the mounted pipette tip 23 from its tip compartment in the tip carrier. The movement of the nozzle 22 may be in any suitable direction, such as, for example, vertically, ie. in the z-direction.

The ejector arm 204 may engage the tips 23 during ejection in any suitable way, while permitting the movement of the arm 12. For example, the ejector arm may have first and second open-ended slots 205 and 207. The first slot 205 has an end portion 206, which may be semi-circular and which is adapted to clear the outer diameter of the first seating portion 30 of the nozzle 22 at all conditions of positional tolerance while being simultaneously small enough to interfere with the shoulder 213 of a corresponding pipette tip 25. The second slot 207 has an end portion 208, which may be semi-circular and which is adapted to clear the outer diameter of the small seating portion 32 of the nozzle at all conditions of positional tolerance while being simultaneously small enough to interfere with the shoulder 215 of a corresponding pipette tip 27. It will be apparent to persons skilled in the art that the slotted member 204 may have more or fewer slots of different sizes to correspond with the number and size of the pipette tips 23 being used.

The ejector arm 204 may extend in a generally horizontal plane. The ejector arm 204 is connected to a drive mechanism (not shown) and controller which control and drive its movement between first and second positions. The ejector system 200 may be configured to provide motion, eg. rotary motion, of the ejector arm 204 in a horizontal plane. Alternatively, in an embodiment that is not shown, the ejector system 200 may be configured to provide linear motion to the ejector arm 204 in a horizontal plane. As another alternative, the ejector system 200 could provide motion to the ejector arm 204 along a path that is not along a horizontal plane.

Figure 11:
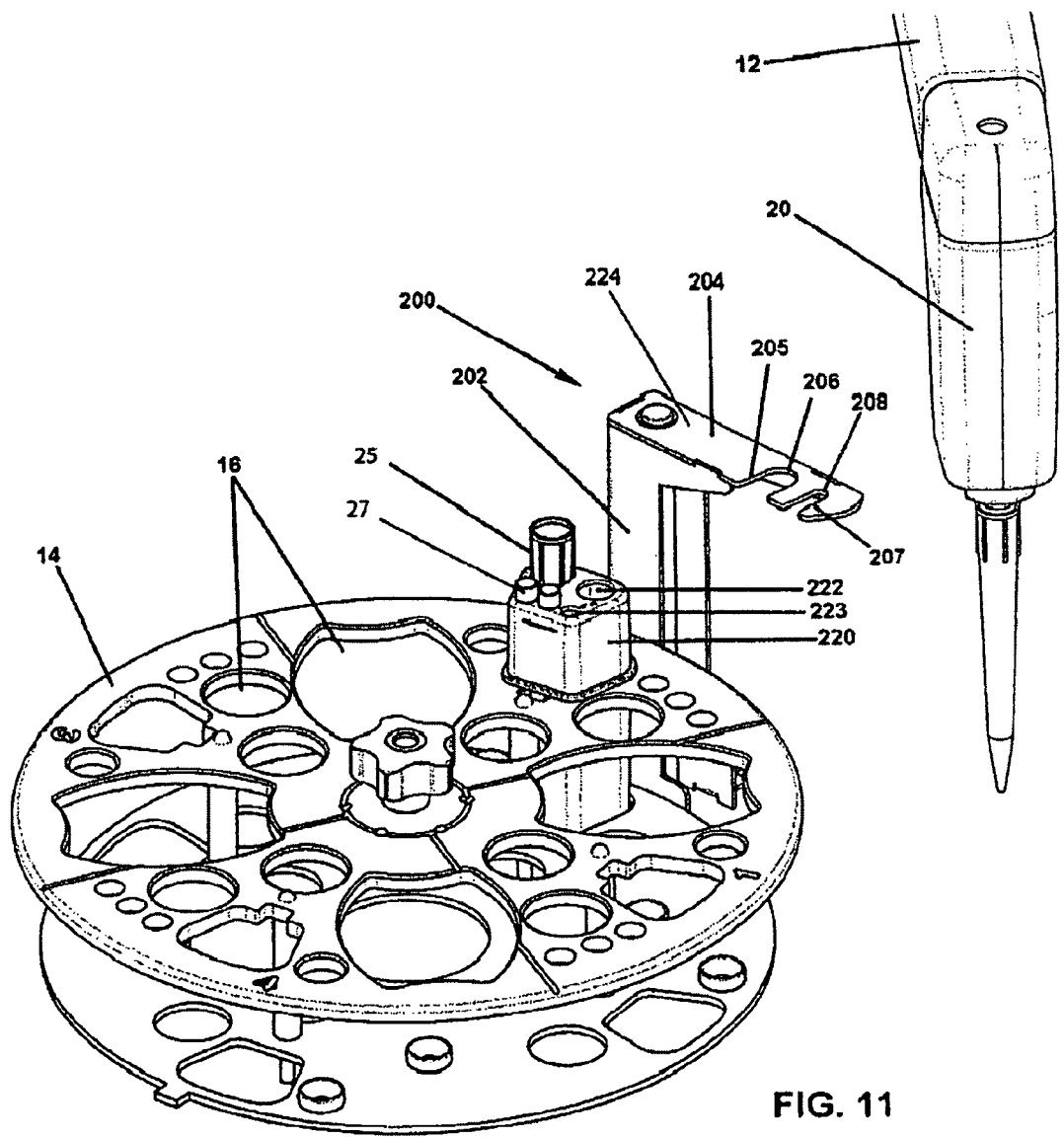
FIG. 11 is an elevation view of components of the pipette machine of FIG. 1, which are involved in the ejection of a disposable pipette tip from the nozzle.

In the embodiment shown in FIG. 11, there is provided an elongate vertical member 202 which is connected to a drive motor or actuator (not shown) that causes the rotation of the vertical member 202 about its axis in response to signals received from the controller (not shown) that operates on programmed instructions. Precise movement and control of the ejector arm 204 may be accomplished by any means known in the art.

The slots 205 and 207 on the ejector arm 204 are positioned such that, by the coordinated movement of the carousel 14 and the ejector arm 200, a selected slot 205 or 207 can be made to be in alignment with the selected tip compartment 222 or 223 on the carousel 14 wherein an imaginary center of the semicircular end 206 or 208 of the slot 205 or 207 intersects a central vertical axis of the tip compartment 222 or 223, as illustrated in FIGS. 14a and 14b respectively. In a particular embodiment, this alignment can occur at the same time as the tip compartment is positioned such that the tip head is able to lower a tip into the compartment.

FIGS. 12a, 12b, 12c and 12d illustrate the ejection of a first pipette tip 25 from the first seating surface 30 of the nozzle 22. FIGS. 13a, 13b, 13c and 13d illustrate the ejection of a second pipette 27 from the second seating surface 32 of the nozzle 22.

Figure 12A:
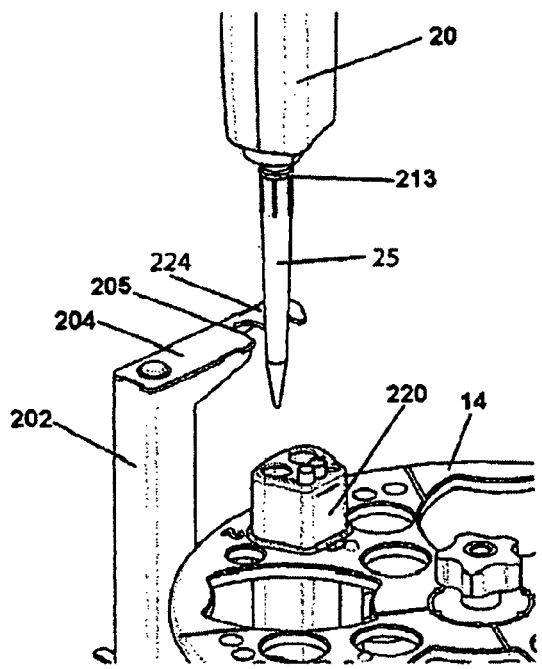
FIGS. 12a, 12b, 12c and 12d are a series of elevation views illustrating tip ejection of a first pipette tip from the pipette nozzle shown in FIG. 1.
Figure 12B:
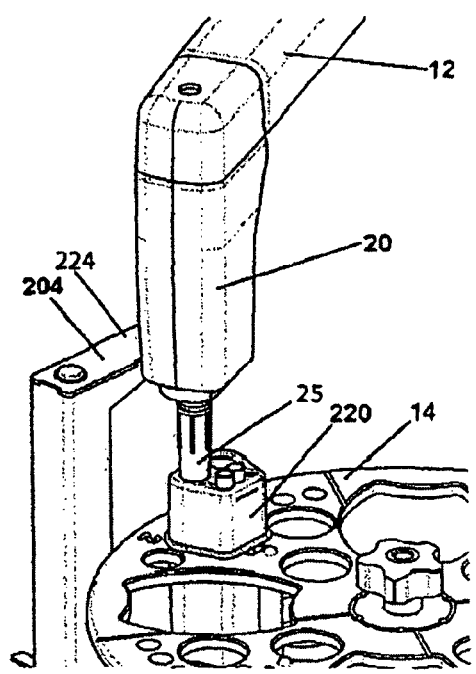
Figure 12C:
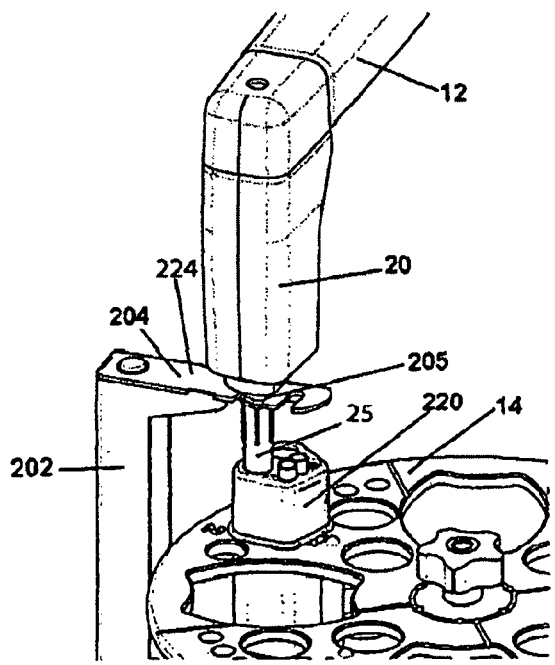
Figure 12D:
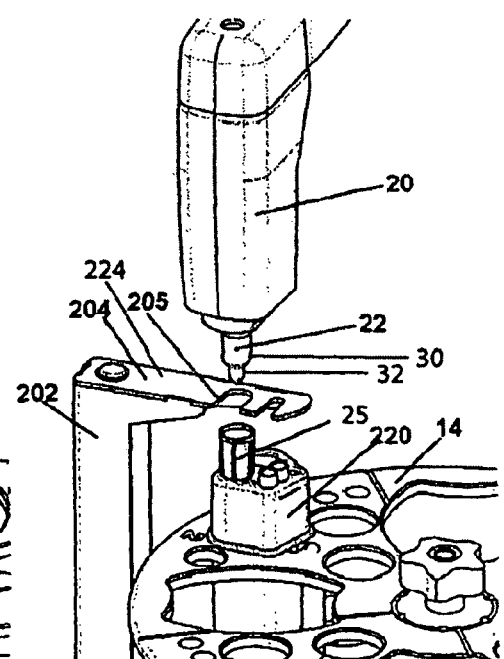
Figure 13A:
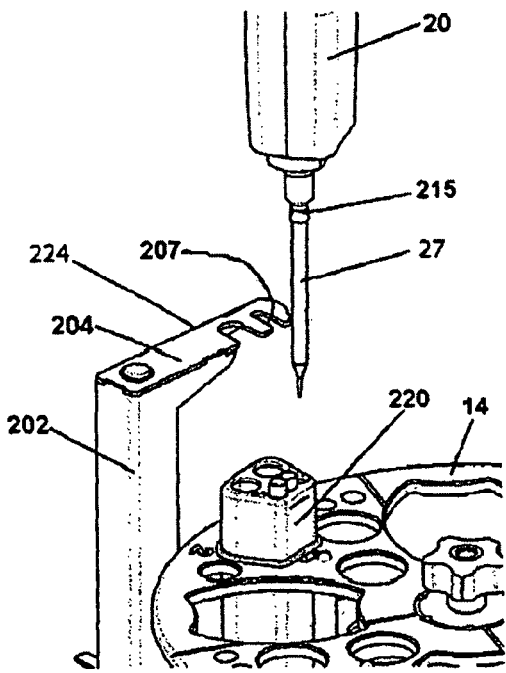
FIGS. 13a, 13b, 13c and 13d are a series of elevation views illustrating tip ejection of a second pipette tip from the pipette nozzle shown in FIG. 1.
Figure 13B:
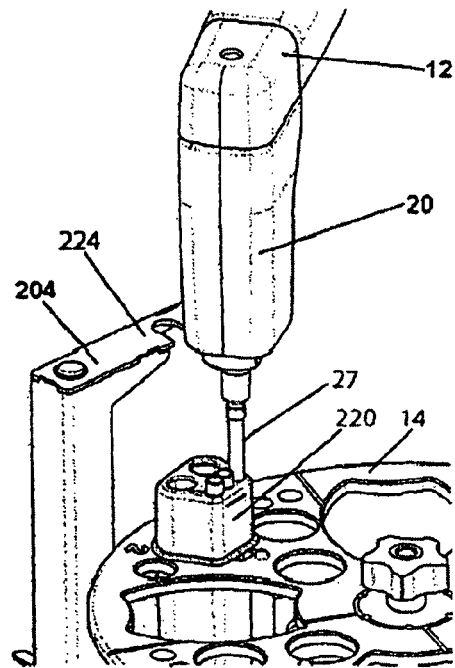
Figure 13C:
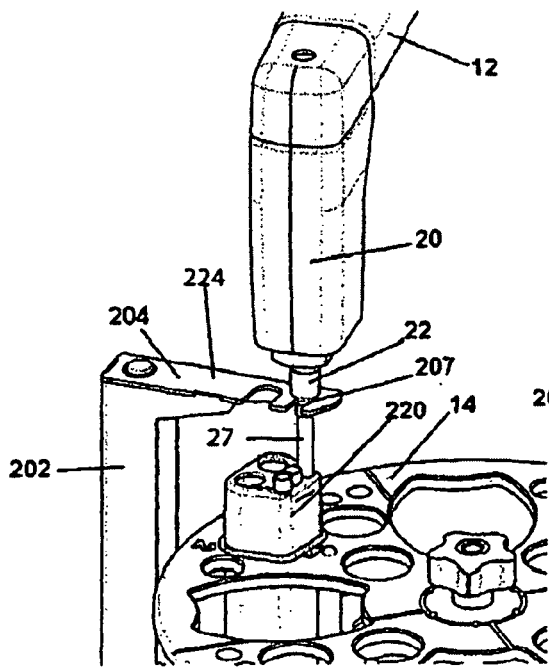
Figure 13D:
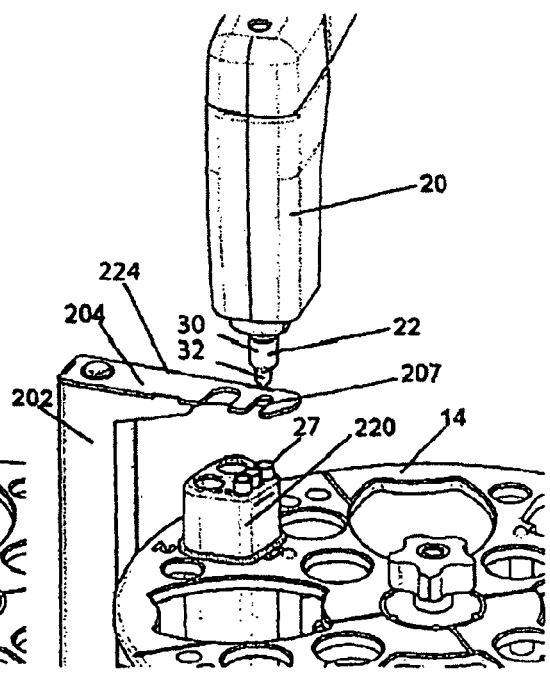

The mounted pipette tip 25 or 27 and a corresponding tip compartment (222 or 223) are brought into alignment by the rotation of the carousel 14 and/or the rotation of the arm 12 such that the longitudinal axis of the tip is centrally aligned with the opening of the tip compartment FIGS. 12a and 13a). The pipette tip 25 or 27 is then lowered partially into the tip compartment 222 or 223 until the shoulder (213 or 215) is slightly below the horizontal plane of the slot (205 or 207) on the ejector arm 204 that corresponds to the size of the pipette tip being used (FIGS. 12b and 13b). The ejector arm 204 is rotated to swing the horizontal member 224 toward the nozzle until the slot (205 or 207) surrounds the nozzle in the region just above the shoulder (213 or 215) of the pipette tip (25 or 27) (FIGS. 12c and 13c). The pipette head 20 is moved vertically upward whereby the horizontal member 224 interferes with the shoulder (213 or 215) of the pipette tip 25 or 27 and dislodges it from the nozzle 22; the pipette tip 25 or 27 falls into the tip compartment 222 or 223 (FIGS. 12d and 13d). The pipette head 20 is able to pick up another pipette tip 25 or 27 if suitable once the ejector arm is withdrawn from the area above the carousel, including the pipette tip that was discharged if reuse of the tip 25 or 27 is suitable.

The pipette tips 25 and 27 have been described as including a shoulder which is engaged by the tip ejector arm of the present invention during tip ejection. It is optionally possible for the tips to be made with shoulders that extend only partially or fractionally around the circumference of the tips, while still functioning to engage the ejector arm during tip ejection.

The described and illustrated embodiment of the tip ejector system 200 is shown used in conjunction with a dual pipette tip nozzle. However, the present invention may be practiced in embodiments that accommodate other configurations of pipette heads and tip nozzles. For example, a tip ejector system in accordance with the present invention may be used where there are two independent tip heads each with a nozzle that accommodates different sized pipette tips but that engages a corresponding notch in the ejector arm during a tip ejecting operation. Also, a tip ejector system in accordance with the present invention may be used in conjunction with a single nozzle tip head by using, for example, an ejector arm with one appropriately dimension slot, or in conjunction with a tip head that accommodates multiple pipette tips of the same size by using a stripping arm with a number of appropriately dimensioned slots that correspond to the number of tips on the tip head and spaced appropriately on the ejector arm so as to engage the shoulder on each tip. Furthermore, the tip ejector system of the present invention may be used in conjunction with a tip head having nozzles that are able to accommodate more than two different sized pipette tips wherein the ejector arm has appropriately sized and positioned notches.

Most automated pipetting robots have three axes of motion to allow the tip head to access the fluid in different containers in a given area. The tip ejector system 200 described herein is used with a θ-z-θ robot where the rotational (θ) and vertical (z) motion of a robot arm holding the tip head is combined with rotational (θ) motion of the carousel to allow the tip head to access a given point on the carousel. Because the tip stripping operations must occur on the carousel where the horizontal arc described by the rotation of end 37 of the tip nozzle intersects the horizontal arcs described by the rotation of the tip stripping slots 205 and 207, rotation of the carousel allows stripping actions to occur at points on circles concentric with the point of rotation of the carousel. However the tip ejector system 200 described herein could alternatively be used with the more common x-y-z gantry style robot (e.g. BioMek FX™, Qiagen™ Biorobots™) where the tip head has one vertical and two orthogonal horizontal axes of motion. For use with an x-y-z robot the ejector arm could rotate as described. Alternatively however, the ejector arm could be made to move linearly in, for example, a horizontal plane.

While the above description constitutes the preferred embodiments, it will be appreciated that the present invention is susceptible to modification and change without departing from the fair meaning of the accompanying claims.

The invention claimed is:

1. A tip ejector system for use on an automated pipette machine to eject a pipette tip from a pipette nozzle on the machine, the tip ejector system comprising:
    an arm that is rotatable in a horizontal plane between a first position and a second position,
    wherein in the first position the arm is positioned to engage the tip during movement of the nozzle along a selected path and to prevent movement of the tip along said selected path while permitting the nozzle to move along said selected path, so that said movement of the nozzle along said selected path causes said nozzle and said tip to disengage from each other,
wherein in the second position the arm is positioned to avoid engagement with the tip during movement of the nozzle,
wherein the arm defines a slot, and
wherein the slot has a selected width that is sufficiently large to fit a first portion of the pipette nozzle and sufficiently small to prevent pass-through of at least one portion of the tip.

2. A tip ejector as claimed in claim 1, wherein the slot is a first slot and said pipette tip is a first pipette tip, and wherein the arm has at least a second slot, wherein the second slot has a different width than the first slot, wherein the second slot has a selected second width that is sufficiently large to fit a second portion of the pipette nozzle and sufficiently small to prevent pass-through of the at least a portion of a second tip.

3. A tip ejector as claimed in claim 1, wherein the automated pipette machine includes a carousel, wherein the carousel has a plurality of pipette receptacles, wherein the first position of the arm is selectable based on the position of the receptacle into which the pipette tip is to be ejected.

4. An automated pipette machine, comprising:
A. a movable carousel having a plurality of pipette receptacles;
B. a movable pipette machine arm with a pipette nozzle, the pipette nozzle including:
a body defining a passage there through; and
at least two seating surfaces on the body, including a first seating surface and a second seating surface,
wherein the first seating surface is configured to receive and sealingly mate with a first size of pipette tip in a manner such that the passage is in fluid communication with the first size of pipette tip,
and wherein the second seating surface is configured to receive and sealingly mate with a second size of pipette tip in a manner such that the passage is in fluid communication with the second size of pipette tip; and
C. a tip ejector system including:
a tip ejector arm that is movable between a first position and a second position, wherein in the first position the tip ejector arm is positioned to engage the tip during movement of the nozzle along a selected path and to prevent movement of the tip along said selected path while permitting the nozzle to move along said selected path, so that said movement of the nozzle along said selected path causes said nozzle and said tip to disengage from each other, and wherein in the second position the tip ejector arm is positioned to avoid engagement with the tip during movement of the nozzle.

5. An automated pipette machine as claimed in claim 4, wherein the tip ejector arm rotates in a horizontal plane between the first and second positions.

6. An automated pipette machine as claimed in claim 5, wherein the tip ejector arm defines a slot, wherein the slot has a selected width that is sufficiently large to fit the first seating surface of the pipette nozzle and sufficiently small to prevent pass-through of at least a portion of the tip.

7. An automated pipette machine as claimed in claim 6, wherein the slot is a first slot and said pipette tip is a first pipette tip, and wherein the tip ejector arm has at least a second slot, wherein the second slot has a different width than the first slot, wherein the second slot has a selected second width that is sufficiently large to fit the second seating surface of the pipette nozzle and sufficiently small to prevent pass-through of the at least a portion of a second tip.

8. An automated pipette machine as claimed in claim 4, wherein the first position of the tip ejector arm is selectable based on the position of the pipette receptacle into which the pipette tip is to be ejected.

* * * * *